（12） United States Patent
LoPresti et al.

(10) Patent No.: US 8,542,841 B2
(45) Date of Patent: Sep. 24, 2013

(54) METHOD TO ESTIMATE THE SOUND PRESSURE LEVEL AT EARDRUM USING MEASUREMENTS AWAY FROM THE EARDRUM

(75) Inventors: Janice LoPresti, Itasca, IL (US); Tao Zhang, Eden Prairie, MN (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 411 days.

(21) Appl. No.: 12/685,295

(22) Filed: Jan. 11, 2010

(65) Prior Publication Data

US 2010/0202642 A1    Aug. 12, 2010

Related U.S. Application Data

(60) Provisional application No. 61/143,820, filed on Jan. 12, 2009.

(51) Int. Cl.
*H04R 25/00* (2006.01)
(52) U.S. Cl.
USPC .............................. 381/60; 381/312; 381/328
(58) Field of Classification Search
USPC ..................... 381/60, 312, 316–319, 321, 328
See application file for complete search history.

(56) References Cited

U.S. PATENT DOCUMENTS

| 3,491,214 A | 1/1970 | Rosemond et al. |
|---|---|---|
| 4,564,955 A | 1/1986 | Birch et al. |
| 4,596,902 A | 6/1986 | Gilman |
| 4,809,708 A | 3/1989 | Geisler et al. |
| 5,386,475 A | 1/1995 | Birck et al. |
| 5,711,308 A | 1/1998 | Singer |
| 5,792,073 A | 8/1998 | Keefe |
| 5,897,494 A | 4/1999 | Flock et al. |
| 5,987,146 A | 11/1999 | Pluvinage et al. |
| 6,007,494 A | 12/1999 | Zenner et al. |
| D431,294 S | 9/2000 | Barnard et al. |
| 6,154,546 A | 11/2000 | Uvacek |
| 6,674,862 B1 | 1/2004 | Magilen |
| D506,258 S | 6/2005 | Nielsen |

(Continued)

FOREIGN PATENT DOCUMENTS

| AU | 5830898 A | 9/1998 |
|---|---|---|
| AU | 2010200103 B2 | 7/2011 |

(Continued)

OTHER PUBLICATIONS

"U.S. Appl. No. 12/130,764, Non-Final Office Action mailed Aug. 20,2010", 8 pgs.

(Continued)

*Primary Examiner* — Suhan Ni
(74) *Attorney, Agent, or Firm* — Schwegman Lundberg & Woessner, P.A.

(57) ABSTRACT

A method for measuring sound pressure at a tympanic membrane of a wearer's ear including a high frequency range with a hearing assistance device. The hearing assistance device comprises a processor connected to a sensor in the ear canal. The device provides a measure of the sound pressure level at the tympanic membrane of the wearer using a null frequency and a null Q measured at a distant position away from the tympanic membrane. The method does not require a precise knowledge of the ear canal, nor does it require an elaborate calibration step. In various embodiments, the present approach works at low and high frequencies.

22 Claims, 7 Drawing Sheets

(56) References Cited

U.S. PATENT DOCUMENTS

| | | | |
|---|---|---|---|
| 6,940,989 B1 | 9/2005 | Shennib et al. | |
| 7,239,711 B1 | 7/2007 | Andersen et al. | |
| 7,599,508 B1 | 10/2009 | Lynch et al. | |
| 7,756,283 B2 | 7/2010 | Bramslow | |
| 7,778,424 B2 | 8/2010 | Lange | |
| 8,059,847 B2 * | 11/2011 | Nordahn | 381/60 |
| 8,315,402 B2 | 11/2012 | Zhang et al. | |
| 8,374,370 B2 | 2/2013 | Zhang et al. | |
| 2002/0085729 A1 | 7/2002 | Marx | |
| 2004/0028250 A1 | 2/2004 | Shim | |
| 2004/0044389 A1 | 3/2004 | Crawford | |
| 2004/0234094 A1 | 11/2004 | Saunders et al. | |
| 2005/0002539 A1 | 1/2005 | Nielsen | |
| 2006/0045282 A1 | 3/2006 | Reber | |
| 2006/0171550 A1 | 8/2006 | Bryant et al. | |
| 2007/0009107 A1 | 1/2007 | Lange | |
| 2007/0217639 A1 | 9/2007 | Stirnemann | |
| 2007/0248237 A1 | 10/2007 | Bren et al. | |
| 2008/0152178 A1 | 6/2008 | Topholm et al. | |
| 2008/0194984 A1 | 8/2008 | Keefe | |
| 2008/0260192 A1 | 10/2008 | Yanz et al. | |
| 2008/0260193 A1 | 10/2008 | Westermann et al. | |
| 2008/0298600 A1 | 12/2008 | Poe et al. | |
| 2009/0245525 A1 | 10/2009 | Zhang et al. | |
| 2009/0245560 A1 | 10/2009 | Zhang et al. | |
| 2009/0299215 A1 | 12/2009 | Zhang | |
| 2010/0246869 A1 | 9/2010 | Zhang et al. | |
| 2010/0260343 A1 | 10/2010 | Recker et al. | |
| 2011/0098551 A1 | 4/2011 | Zhang | |

FOREIGN PATENT DOCUMENTS

| | | |
|---|---|---|
| AU | 2010201189 | 9/2011 |
| AU | 2009201227 B2 | 10/2011 |
| AU | 2009201228 B2 | 1/2012 |
| AU | 2009280002 B2 | 10/2012 |
| DE | 4327634 C1 | 6/1994 |
| EP | 0381608 A2 | 8/1990 |
| EP | 1448014 B1 | 10/2005 |
| EP | 1705950 A2 | 9/2006 |
| EP | 2107831 A2 | 10/2009 |
| EP | 2323553 B1 | 10/2012 |
| WO | WO-8901315 A1 | 2/1989 |
| WO | WO-9931936 A1 | 6/1999 |
| WO | WO-0239784 A1 | 5/2002 |
| WO | WO-2005089016 A1 | 9/2005 |
| WO | WO-2007045254 A1 | 4/2007 |
| WO | WO-2007045271 A1 | 4/2007 |
| WO | WO 2008/017326 * | 2/2008 |
| WO | WO-2010016925 A1 | 2/2010 |

OTHER PUBLICATIONS

"U.S. Appl. No. 12/130,764, Preliminary Amendment mailed Jul. 21, 2008", 6 pgs.

"U.S. Appl. No. 12/130,764, Response filed Jul. 30, 2010 to Restriction Requirement mailed Jul. 29, 2010", 7 Pgs.

"U.S. Appl. No. 12/130,764, Restriction Requirement mailed Jul. 29, 2010", 9 pgs.

"U.S. Appl. No. 12/980,745, Preliminary Amendment mailed Feb. 14, 2011", 5 pgs.

"Australian Application Serial No. 2010200103, First Examiner Report mailed Feb. 2, 2011", 2 pgs.

"International Application Serial No. PCT/US2009/004528, Search Report mailed Oct. 13, 2009", 7 pgs.

"International Application Serial No. PCT/US2009/004528, Written Opinion mailed Oct. 13, 2009", 7 pgs.

Chan, C K, et al., "Estimation of Eardrum Acoustic Pressure and of Ear Canal Length From Remote Points in the Canal Length From Remote Points in the Canal", Journal of the Acoustical Society of America, vol. 87, No. 3, XP009035813 ISSN: 0001-4966, (Mar. 1, 1990), 1237-1247.

Hudde, H, et al., "Methods for Estimating the sound pressure at the eardrum", Journal of the Acoustical Society of America, vol. 106, No. 4, XP012001248 ISSN: 0001-4966, (Oct. 1, 2009), 1977-1992.

Pascal, Jerome, et al., "Linear and nonlinear model of the human middle ear", J. Acoust. Soc. Am. vol. 104, No. 3, Pt. 1, (Sep. 1998), pp. 1509-1516.

"U.S. Appl. No. 12/102,602, Final Office Action mailed Aug. 24, 2012", 7 pgs.

"U.S. Appl. No. 12/102,602, Non Final Office Action mailed Apr. 4, 2012", 7 pgs.

"U.S. Appl. No. 12/102,602, Notice of Allowance mailed Jan. 25, 2013", 5 pgs.

"U.S. Appl. No. 12/102,602, Response filed to Restriction Requirement mailed Dec. 8, 2011", 8 pgs.

"U.S. Appl. No. 12/102,602, Response filed Jul. 2, 2012 to Non Final Office Action mailed Apr. 4, 2012", 11 pgs.

"U.S. Appl. No. 12/102,602, Response filed Dec. 26, 2012 to Final Office Action mailed Aug. 24, 2012", 8 pgs.

"U.S. Appl. No. 12/102,602, Restriction Requirement mailed Nov. 8, 2011", 6 pgs.

"U.S. Appl. No. 12/414,876, Non Final Office Action mailed Aug. 12, 2011", 8 pgs.

"U.S. Appl. No. 12/414,876, Notice of Allowance mailed Jan. 11, 2012", 5 pgs.

"U.S. Appl. No. 12/414,876, Notice of Allowance mailed Oct. 11, 2012", 5 pgs.

"U.S. Appl. No. 12/414,876, Response filed Dec. 12, 2011 to Non Final Office Action mailed 08/1/2/11", 9 pgs.

"U.S. Appl. No. 12/414,889, Non Final Office Action mailed Dec. 15, 2011", 11 pgs.

"U.S. Appl. No. 12/414,889, Notice of Allowance mailed Jul. 18, 2012", 7 pgs.

"U.S. Appl. No. 12/414,889, Response filed Jun. 14, 2012 to Non Final Office Action mailed Dec. 15, 2011", 9 pgs.

"U.S. Appl. No. 12/537,908, Response filed Jan. 11, 2012 to Non Final Office Action mailed Oct. 11, 2011", 9 pgs.

"U.S. Appl. No. 12/537,908, Final Office Action mailed Mar. 15, 2012", 11 pgs.

"U.S. Appl. No. 12/537,908, Non Final Office Action mailed Oct. 9, 2012", 12 pgs.

"U.S. Appl. No. 12/537,908, Non Final Office Action mailed Oct. 11, 2011", 10 pgs.

"U.S. Appl. No. 12/537,908, Preliminary Amendment mailed Jun. 22, 2010", 3 pgs.

"U.S. Appl. No. 12/537,908, Response filed Jan. 9, 2013 to Non Final Office Action mailed Oct. 9, 2012", 9 pgs.

"U.S. Appl. No. 12/537,908, Response filed Sep. 12, 2012 to Final Office Action mailed Mar. 15, 2012", 9 pgs.

"U.S. Appl. No. 12/730,380, Response filed Jan. 11, 2013 to Final Office Action mailed Oct. 11, 2012", 7 pgs.

"U.S. Appl. No. 12/730,380, Final Office Action mailed Oct. 11, 2012", 10 pgs.

"U.S. Appl. No. 12/730,380, Non Final Office Action mailed Feb. 7, 2013", 13 pgs.

"U.S. Appl. No. 12/730,380, Non Final Office Action mailed Mar. 30, 2012", 10 pgs.

"U.S. Appl. No. 12/730,380, Response filed Aug. 30, 2012 to Non Final Office Action mailed Mar. 30, 2012", 7 pgs.

"U.S. Appl. No. 12/980,745, Non Final Office Action mailed Jan. 18, 2013", 11 pgs.

"Australian Application Serial No. 2009201227, First Examiner Report mailed Apr. 20, 2010", 2 Pgs.

"Australian Application Serial No. 2009201227, Response filed Apr. 18, 2011 to First Examiner Report mailed Apr. 20, 2010", 9 pgs.

"Australian Application Serial No. 2009201228, First Examiner Report mailed Apr. 23, 2010", 1 pg.

"Australian Application Serial No. 2009201228, Office Action Response Filed Aug. 3, 2011", 5 pgs.

"Australian Application Serial No. 2009280002, Office Action Response Filed Sep. 17, 2012", 13.

"Australian Application Serial No. 2010200103, Response filed Jul. 8, 2011 to First Examiner Report mailed Feb. 2, 2011", 5 pgs.

"Australian Application Serial No. 2010201189, Examiner Report mailed Mar. 11, 2011", 1 pg.

"Australian Application Serial No. 2010201189, Response filed May 19, 2011 to Examiner Report mailed Mar. 11, 2011", 1 pg.

"Australian Application Serial No. 2009201228, Subsequent Examiner Report mailed Jun. 23, 2011", 2 pgs.

"Australian Application Serial No. 2009280002, Office Action Mailed Mar. 23, 2012", 2 Pgs.

"European Application Serial No. 08251441.5, Extended Search Report mailed Dec. 20, 2011", 18 pgs.

"European Application Serial No. 08251441.5, Response filed Jul. 5, 2012 to Extended Search Report mailed Dec. 20, 2011", 15 pgs.

"European Application Serial No. 09250957.9, Extended European Search Report mailed Dec. 13, 2010", 5 pgs.

"European Application Serial No. 09250957.9, Response filed Jul. 5, 2011 to Extended European Search Report mailed Dec. 13, 2010", 16 pgs.

"European Application Serial No. 09250958.7, Extended European Search Report mailed Nov. 29, 2010", 5 pgs.

"European Application Serial No. 09250958.7, Response filed Jun. 24, 2011 to Extended European Search Report mailed Nov. 29, 2010", 5 pgs.

"European Application Serial No. 10250039.4, Examination Report mailed Jan. 16, 2013", 4 pgs.

"European Application Serial No. 10250039.4, Extended Search Report mailed Apr. 16, 2012", 8 pgs.

"European Application Serial No. 10250039.4, Response filed Nov. 16, 2012 to Extended Search Report mailed Apr. 16, 2012", 10 pgs.

"European Application Serial No. 10250568.2, Extended Search Report mailed Dec. 13, 2011", 8 pgs.

"European Application Serial No. 10250568.2, Office Action mailed Jan. 16, 2012", 2 pgs.

"European Application Serial No. 10250568.2, Response filed Jul. 10, 2012 to Extended Search Report mailed Dec. 13, 2011", 11 pgs.

"European Application Serial No. 08251441.5, Partial European Search Report mailed Jul. 14, 2011", 5 pgs.

"International Application Serial No. PCT/US2009/004528, International Preliminary Report on Patentability mailed Feb. 17, 2011", 6 pgs.

Dillon, Ph.D., Harvey, "Hearing Aids", 4.4 Practical Issues in Real-Ear Testing, (Jan. 1, 2001), 101-104.

Moodie, K Shane, et al., "Procedure for Predicting Real-Ear Hearing Aid Performance in Young Children", Am. Journal of Audiology, Am. Speech-Language-Hearing Association, 3(1), (Mar. 1, 1994), 23-31.

Munro, Kevin J, et al., "Measuring the Real-Ear to Coupler Difference Transfer Function with and Insert Earphone and a Hearing Instrument: Are they the same?", Ear and Hearing, 26(1), (Feb. 1, 2005), 27-34.

Rutten, "The us of SQUID magnetometer for middle ear research", Cryogenics, (1982), 457-460.

Yanz, Jerry, et al., "Real Ear Measurement System Using Thin Tube", U.S. Appl. No. 60/912,343, filed Apr. 17, 2007, 19 pgs.

\* cited by examiner

METHOD TO ESTIMATE THE SOUND PRESSURE LEVEL AT EARDRUM USING MEASUREMENTS AWAY FROM THE EARDRUM

RELATED APPLICATION

The present application claims the benefit under 35 U.S.C. 119(e) of U.S. Provisional Patent Application Ser. No. 61/143,820, filed on Jan. 12, 2009, which is incorporated herein by reference in its entirety.

FIELD OF TECHNOLOGY

This application relates generally to hearing assistance devices and more particularly to a method for estimating sound pressure level at a wearer's eardrum from sound at another ear canal location.

BACKGROUND

Hearing assistance devices, including hearing aids, are electronic devices that provide signal processing functions such as wide dynamic range compression and output compression limiting control. In many hearing assistance devices these and other functions can be programmed to fit the requirements of individual users. Performance of a user's hearing assistance device, while the device is in the user's ear, is difficult to verify. Furthermore, methods that apply at low frequencies may well not work at high frequencies. The expense of measurement equipment, the time it takes to make the measurements, and the perceived complexity of the procedure, have all proven to be obstacles to widespread use of such measurements. However, such measurements may enable better programming of a user's hearing assistance device because each user's ear is different.

SUMMARY

This document provides method and apparatus for estimating the sound pressure level at a user's tympanic membrane, or eardrum. One method uses a hearing assistance device with a sound sampling apparatus that provides measurements at a first position in the ear canal to generate the sound pressure level at the eardrum of the wearer. This system does not require precise knowledge of the ear canal. Furthermore, it does not require cumbersome calibration steps for each patient, which is critical for practical and efficient real-ear measurement in the clinical environment. In one embodiment, the present approach is implemented in the fitting software and the hearing device. In alternate embodiments, the present method is implemented completely in the hearing device. In various embodiments, the present approach works at low and high frequencies.

In various embodiments, the present subject matter provides a method for measuring an estimated sound pressure level at a tympanic membrane in an ear canal of an ear of a wearer of a hearing assistance device using measurements away from the tympanic membrane, the method comprising: placing a sound sampling apparatus in the ear canal at a first position; placing a sound emitter in the ear canal at a second position; generating sound with the sound emitter and receiving sound with the sound sampling apparatus to measure an amplitude response of the ear canal; and determining the estimated sound pressure level at the tympanic membrane using measurements of sound from the sound sampling apparatus and the measured amplitude response. In various embodiments, the method further comprises: determining an amplitude null at a null frequency detected by the sound sampling apparatus at the first position; determining a null Q from the null frequency; determining a modeled sound pressure level at the tympanic membrane and a modeled sound pressure level at the first position using the null frequency and the null Q; and determining the estimated sound pressure level at the tympanic membrane using measurements of sound from the sound sampling apparatus at the first position, the modeled sound pressure levels at the tympanic membrane, and the modeled sound pressure levels at the first position.

Variations of the foregoing methods include wherein placing a sound sampling apparatus comprises placing a thin tube with an end at the first position for sampling sound at the first position. Variations further include placing a second end of the thin tube in a microphone port of the hearing assistance device. Variations include wherein placing a sound sampling apparatus comprises placing a microphone at the first position. In some variations the sound sampling apparatus is a microphone fitted with a small sound tube and wherein the sound emitter is a receiver. In some embodiments the first position and the second position have a minimum distance of about 5 mm. Different ways of emitting sound include, but are not limited to playing a swept audio sound into the ear canal by the hearing assistance device or playing a tone complex into the ear canal by the hearing assistance device.

In some embodiments the null Q is determined by dividing the null frequency by a measured width of the amplitude response at the null frequency.

In some embodiments the method further includes modeling the ear canal as a cascade of cylindrical tubes, each tube of the cascade of tubes having a radius and a length, the cascade of tubes including two middle lengths L1 and L2 which are calculated from: $L1+L2=(5.81\times 10 5-\text{Square Root}[3.38\times 10 11-7.92\times 10 7\times(8450-f_o)])/(3.96\times 10 7)$, where $f_o$ is the null frequency; and estimating a series resistance, R, in a middle ear analog using: $R=(5.92\times 10-3-\text{Square Root}[3.50\times 10-5+1.29\times 10-6\times(2.78-Q)])/(6.46\times 10-7)$, where Q is the null Q.

Various embodiments include estimating the decibels (dB) of sound pressure level (SPL) at the tympanic membrane (TM) from: Estimated dB SPL at TM=Actual dB SPL at the first position+(Modeled dB SPL at TM−Modeled dB SPL at the first position).

This Summary is an overview of some of the teachings of the present application and is not intended to be an exclusive or exhaustive treatment of the present subject matter. Further details about the present subject matter are found in the detailed description and the appended claims. The scope of the present invention is defined by the appended claims and their legal equivalents.

DETAILED DESCRIPTION

The following detailed description of the present invention refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

The sound field in an individual's ear canal is generally more uniform when subjected to low frequency sound because of the longer wavelength. Because of the uniformity, it is assumed that sound pressure levels and phase sensed near the eardrum provide an accurate measure of the sound pressure level and phase at the eardrum. However, the sound field becomes less uniform and more complex as the eardrum and ear canal are subjected to higher frequency sounds. It is risky and uncomfortable, to measure the sound pressure level at the eardrum by placing a sensor very close to the eardrum. Furthermore, it is difficult to predict the sound pressure level at the eardrum without placing a sensor very close to the eardrum at high frequencies.

The present invention relates to a system for measuring the sound pressure level at the eardrum by measurement of sound at another location in the ear canal that is easier to reach. The inventors of the present subject matter discovered in their research that the sound pressure level at the eardrum could be accurately estimated by the sound pressure measurement, measurements of the primary null frequency and null Q of the ear canal at a given location away from the eardrum. These measurements are used to estimate the parameters of an electroacoustic analog model of the ear canal. That model can be used to produce the sound pressure level at the wearer's eardrum based on the sound pressure level at the distant location. This discovery provides a practical way for more accurate measurement of the sound pressure level at the eardrum in devices which can be deployed in hearing assistance devices, such as hearing aids, offered to consumers. Furthermore, this method doesn't require precise knowledge of the individual's ear canal, which makes it feasible for actual products in the field. Thus, an individualized approach is provided to estimating the sound produced at the tympanic membrane of the wearer.

Figure 1:
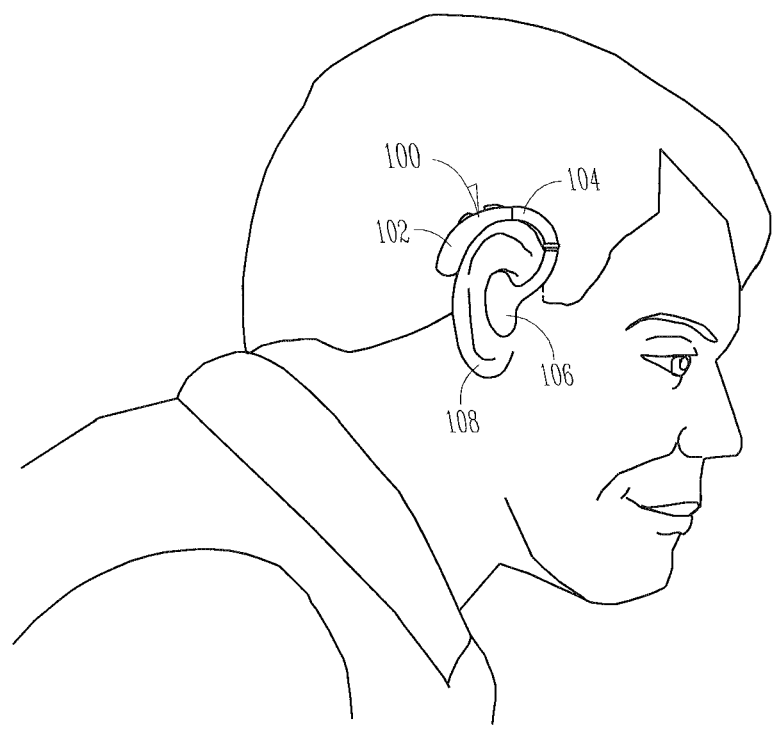
FIG. 1 shows a hearing assistance device worn by a person which is adapted to measure sound at the wearer's eardrum by measuring sound at another location in the wearer's ear canal, according to one embodiment of the present subject matter.

FIG. 1 shows a hearing assistance device worn by a person which is adapted to measure sound at the wearer's eardrum by measuring sound at another location in the wearer's ear canal, according to one embodiment of the present subject matter. The hearing aid 100 shown in FIG. 1 has electronics in a housing 102 placed behind the wearer's ear or over the wearer's ear 108. Such devices include, but are not limited to, behind the ear devices which have receivers (also known as speakers) situated in the housing that contains the electronics. Such devices have ear hooks and sound tubes for delivery of sound from the receiver to the wearer's ear. Such devices also include receiver in the ear designs that have a receiver placed in the ear canal which is connected via wires to the electronics disposed in the housing worn behind or over the ear, such as receiver-in-canal (RIC) or receiver-in-the-ear (RITE) devices. These variations are generally shown as apparatus 104 which is placed in or about the ear canal 106 of the wearer.

Although demonstrated as a behind the ear or over the ear realization of the technology, it is understood that other types of hearing assistance devices can use the present subject matter, including, but not limited to, in-the-ear (ITE), in-the-canal (ITC), or completely-in-the-canal (CIC) type hearing aids. It is understood that other hearing assistance devices not expressly stated herein may fall within the scope of the present subject matter.

Figure 2:
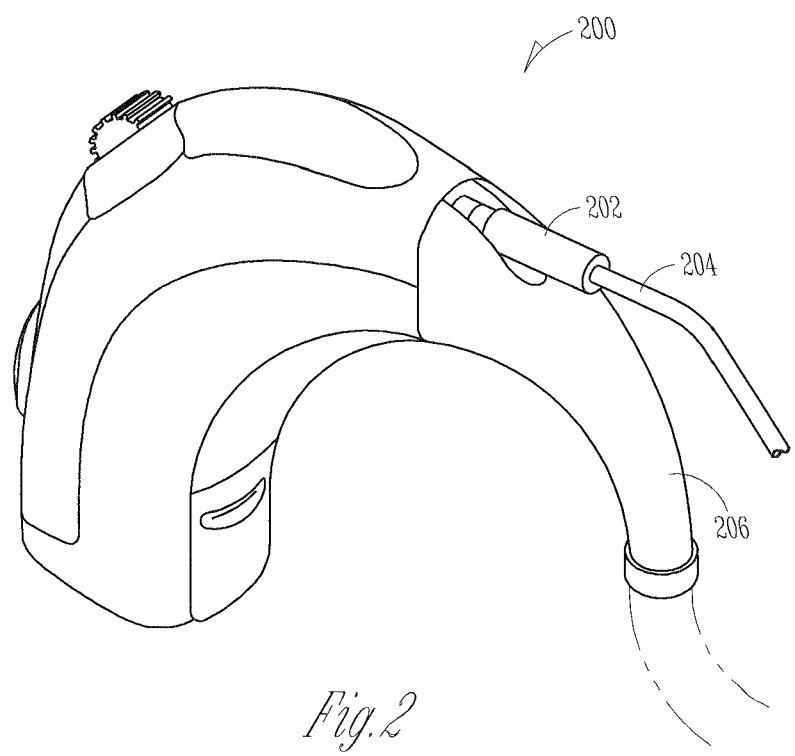
FIG. 2 shows a sound sampling apparatus using a thin tube, according to one embodiment of the present subject matter.
Figure 3:
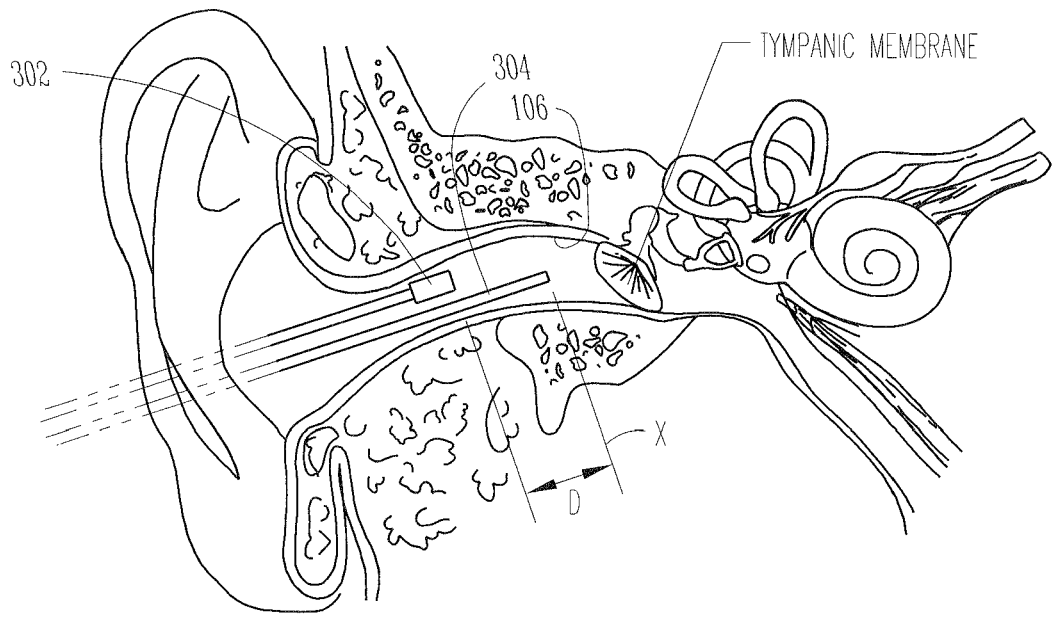
FIG. 3 shows some detail of an example of the sampling apparatus in the ear canal, according to various embodiments of the present subject matter.

Various different sound sampling approaches can be implemented. One type of sound sampling approach is to use a thin sound tube 204 interfaced to a microphone of the hearing assistance device 200. In designs where the microphone is in the housing behind or on the ear, the coupling can be accomplished using a thin tube having a fitting connected to its proximal end that is placed in a microphone port 202 of the device 200, as is shown in FIG. 2 which is one embodiment of a sound sampling apparatus. FIG. 3 shows some detail of an example of the sampling apparatus in the ear canal according to various embodiments of the present subject matter. The distal end of the thin sound tube 304 (shown at position X in FIG. 3) is placed within the ear canal of the wearer 106. In various embodiments, the distal end of the thin tube is placed a distance D from the emitted sound field of the sound tube or receiver in the ear canal. The sound emitter is shown generally to be emitter 302 in the ear canal 106 in FIG. 3. In various embodiments, the minimum distance D is about 5 mm. Other distances are possible without departing from the scope of the present subject matter.

Figure 4:
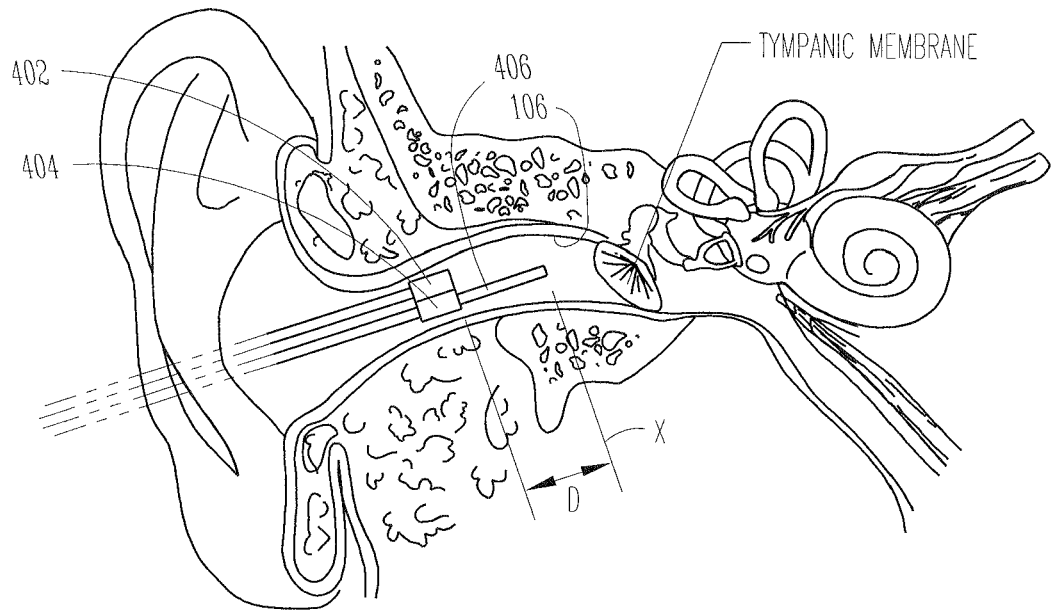
FIG. 4 shows an example of the sampling apparatus in the ear canal, according to various embodiments of the present subject matter.

Another type of sound sampling approach is to use a microphone disposed in the ear canal. Such designs may be implemented in designs with sound delivery tubes or with receivers placed in the canal. Regardless of the particular implementation, the microphone is placed a distance from the sound emitter (tube or receiver). In various embodiments, the minimum distance is about 5 mm. Other distances are possible without departing from the scope of the present subject matter. In one embodiment of the present subject matter, a microphone 404 is fitted with a small sound tube 406 to provide the distance from the sound emitter 402, as demonstrated in FIG. 4.

Regardless of the approach used to measure sound and the particular hearing assistance device configuration, the sound is measured at a location away from the eardrum of the wearer and is used to generate a model of the wearer's ear canal, which in turn is used to calculate the sound pressure level at the eardrum.

Figure 5:
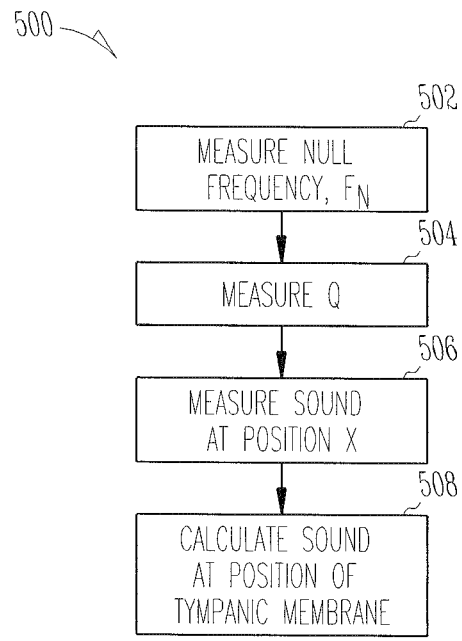
FIG. 5 illustrates one method for measuring sound at the tympanic membrane of the wearer, according to one embodiment of the present subject matter.
Figure 6:
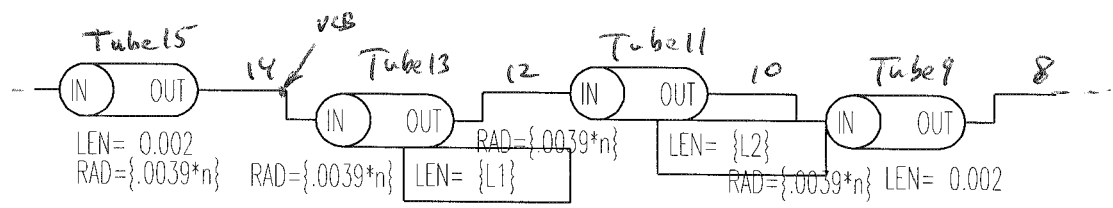
FIG. 6 is a PSPICE model of the ear canal analog, according to one embodiment of the present subject matter.
Figure 7:
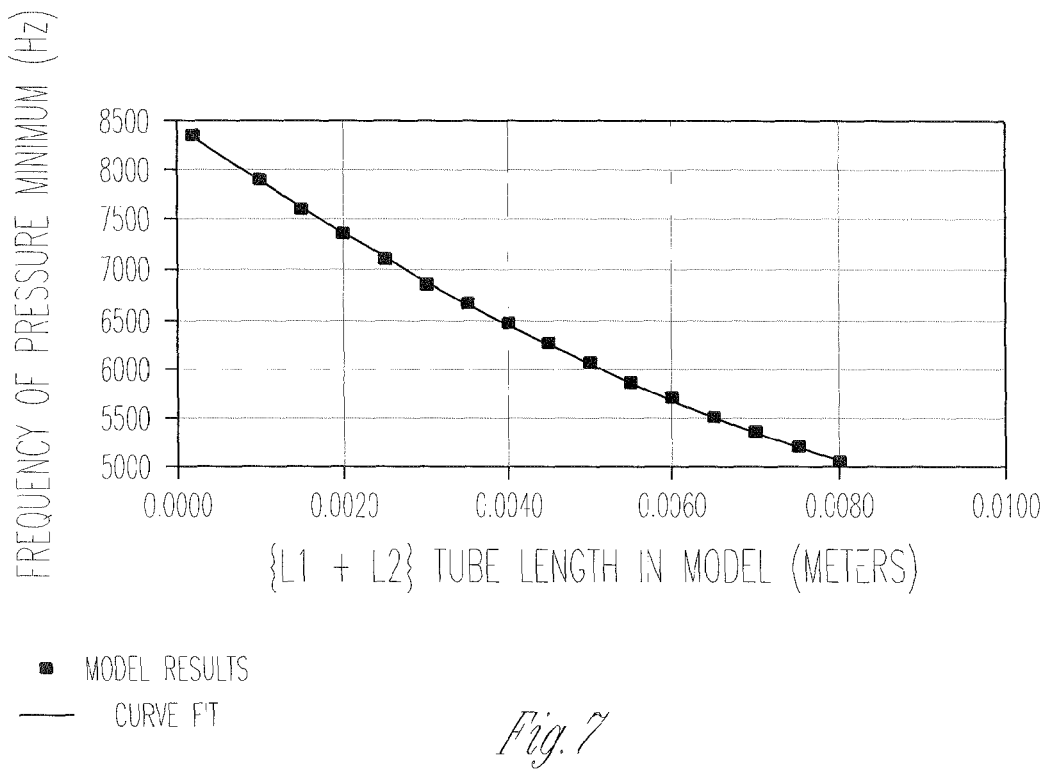
FIG. 7 is a graph of frequency of pressure minimum versus the tube length in the model according to one embodiment of the present subject matter.

FIG. 5 illustrates one method for measuring sound at the tympanic membrane of the wearer, according to one embodiment of the present subject matter. The sound measurement apparatus is placed in the ear canal of the wearer at canal position X. Sound is generated to determine the frequency at which the primary amplitude null occurs at position X (502), called the "null frequency" or Fn or $f_0$. In one embodiment, the sound is a swept audio sound played into the ear canal by the hearing assistance device. In one embodiment, the sound is a tone complex played into the ear canal by the hearing assistance device. Other sounds may be employed without departing from the scope of the present subject matter. A "null Q" of the ear canal as measured at position X is determined (504). In one embodiment, the null Q is obtained by dividing the null frequency by a measured width of the amplitude response at the null (as provided by the 3 dB levels of the amplitude response at the null). Once the null Q and the null frequency are determined, they are used to estimate the model parameters as set forth herein. In one approach the tube length is estimated using the null frequency and the series resistance in the middle ear analog is estimated by matching the measured Q value with the modeled Q value as follows:

(1) TUBE LENGTH: In one embodiment, the tube length can be estimated by matching the measured null frequency and the modeled null frequency as shown in FIG. 6. FIG. 6 is a PSPICE model of the ear canal analog, according to one embodiment of the present subject matter. In FIG. 6, the ear canal is modeled as a cascade of cylindrical tubes, which are defined by its radius (Rad) and length (Len). The middle two lengths L1 and L2 are allowed to change. By adjusting the sum of L1+L2 then we can estimate the proper individualized ear canal values. To reduce the computational cost in practice, the tube length (L1+L2) can be calculated using the following formula: $L1+L2=(5.81\times10^5-\text{Square Root}[3.38\times10^{11}-7.92\times10^7\times(8450-f_0)])/(3.96\times10^7)$, where $f_0$ is the null frequency. FIG. 7 is a graph of frequency of pressure minimum versus the tube length in the model according to one embodiment of the present subject matter. It demonstrates the model results (denoted by squares) and the curve fit (line).

Figure 8:
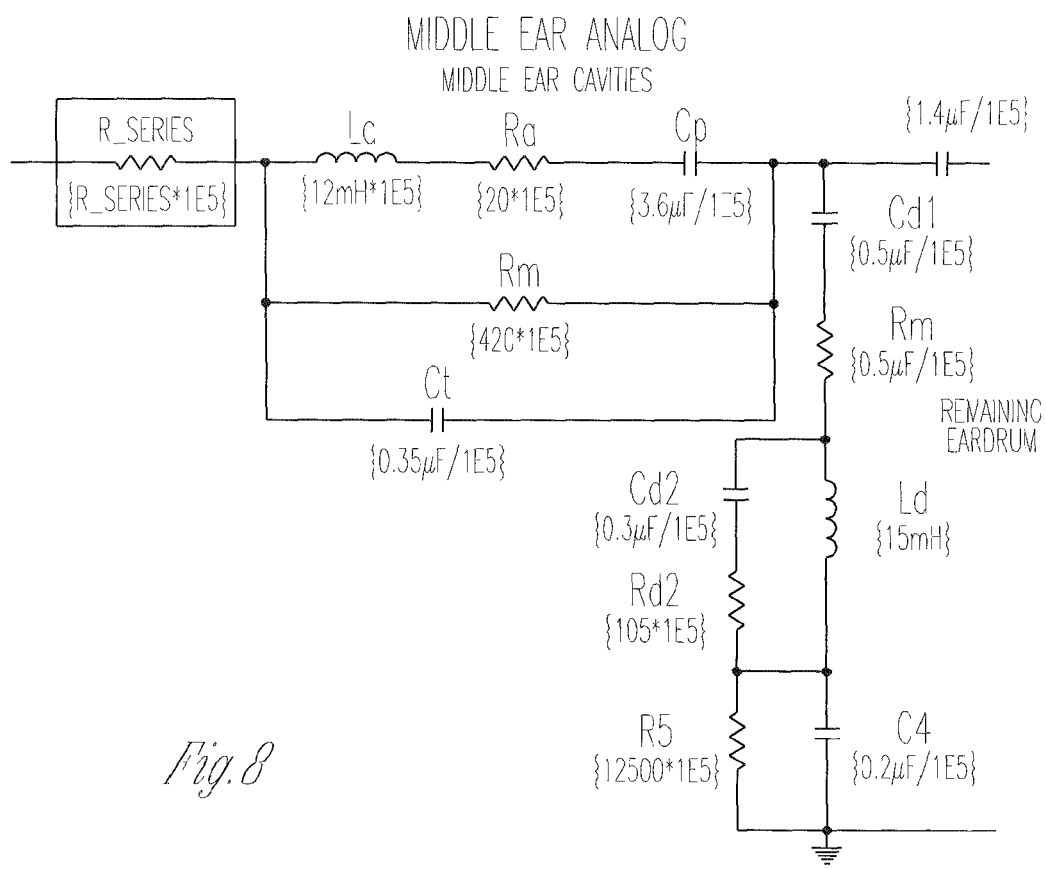
FIG. 8 is a middle ear analog showing a series resistance which is used in one process, according to one embodiment of the present subject matter.

(2) SERIES RESISTANCE: In one embodiment, the series resistance in the middle ear analog is estimated by matching the measured Q value and the modeled Q value as shown in the following figure using the middle ear analog from Pascal, Jerome and Bourgeade, Antoine (1998). "Linear and nonlinear model of the human ear," J. Acoust. Soc. Am. 104 (3) 1509, which is incorporated by reference in its entirety herein and is referenced herein as "Pascal et al, 1998." The middle ear analog as demonstrated by FIG. 8 is taken from Pascal et al, 1998. FIG. 8 is a middle ear analog showing a series resistance which is used in one process, according to one embodiment of the present subject matter. In the model of FIG. 8, the effective area of the eardrum is about 0.55 cm$^2$, the total area is about 0.85 cm$^2$, the thickness is about 0.01 cm (1.1 gm/cm$^3$), and total mass is about 9.35 mg. Other dimensions and masses may be modeled without departing from the scope of the present subject matter and the numbers provided herein are intended to be demonstrative and not exhaustive or exclusive or otherwise limiting.

Figure 9:
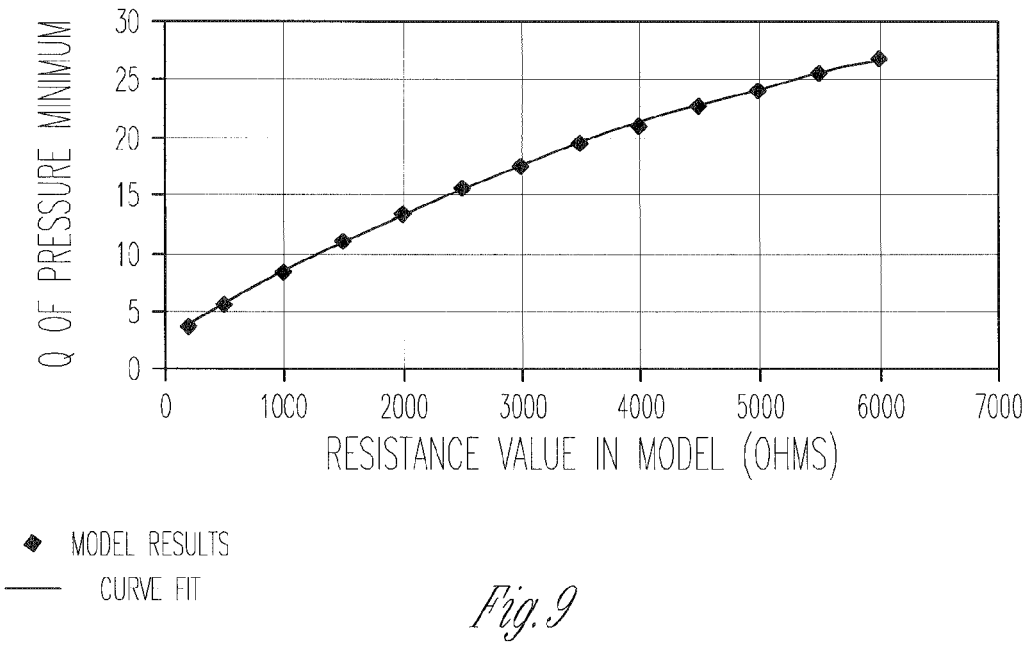
FIG. 9 is a graph of the null Q versus the series resistance according to one embodiment of the present subject matter.

To reduce the computational cost in practice, the series resistance can be calculated using the following formula: $R=(5.92\times10^{-3}-\text{Square Root}[3.50\times10^{-5}+1.29\times10^{-6}\times(2.78-Q)])/(6.46\times10^{-7})$, where Q is the null Q. FIG. 9 is a graph of the null Q versus the series resistance according to one embodiment of the present subject matter. The model results (shown as diamonds) and curve fit (line) are shown.

FIG. 5 illustrates one method for measuring sound at the tympanic membrane of the wearer, according to one embodiment of the present subject matter. Sound is measured at position X (506). The sound at the tympanic membrane is determined as a function of the sound sampled by the sound measurement apparatus at position X, the null frequency and Q, (508). In one embodiment, the formula to produce the sound pressure level at the tympanic membrane is:

$$\text{Estimated dB SPL at TM} = \text{Actual dB SPL at position } X + [\text{Modeled dB SPL at TM} - \text{Modeled dB SPL at position } X].$$

Figure 10:
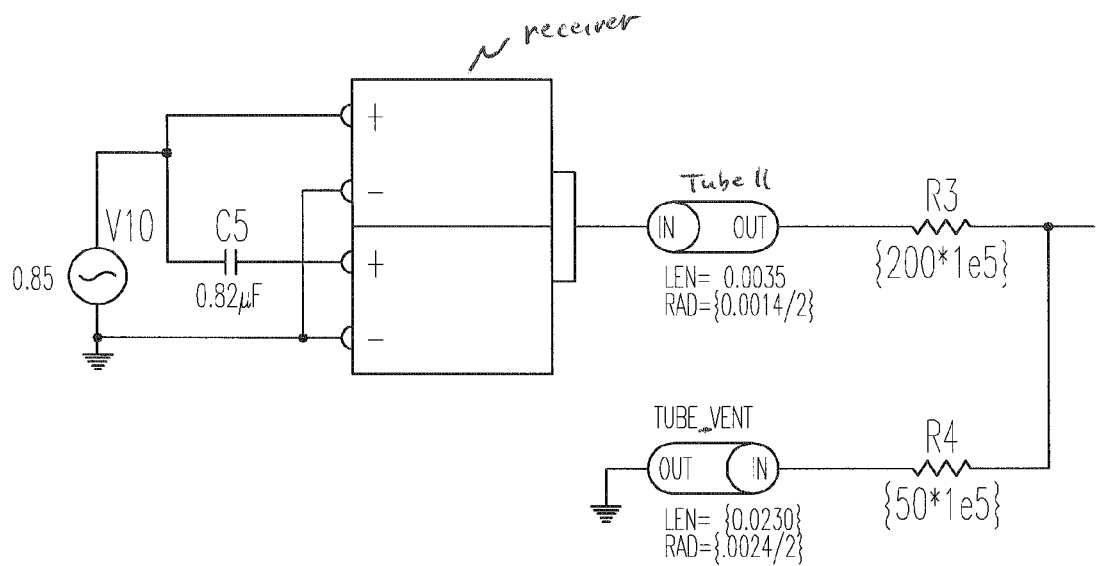
FIG. 10 is a PSPICE model of the ear probe analog which models the device plus the probe, according to one embodiment of the present subject matter.

A detailed model is demonstrated as shown in FIG. 10. The ear probe analog of FIG. 10 is a PSPICE model which models the device plus the probe according to one embodiment of the present subject matter. Therefore, in one embodiment it models: a Knowles receiver (TWFK30017) (which is just one example of a receiver, thus other receivers may be modeled without departing from the teachings of the present application), a receiver tubing, and a probe tube that was threaded through a vent.

Figure 11:
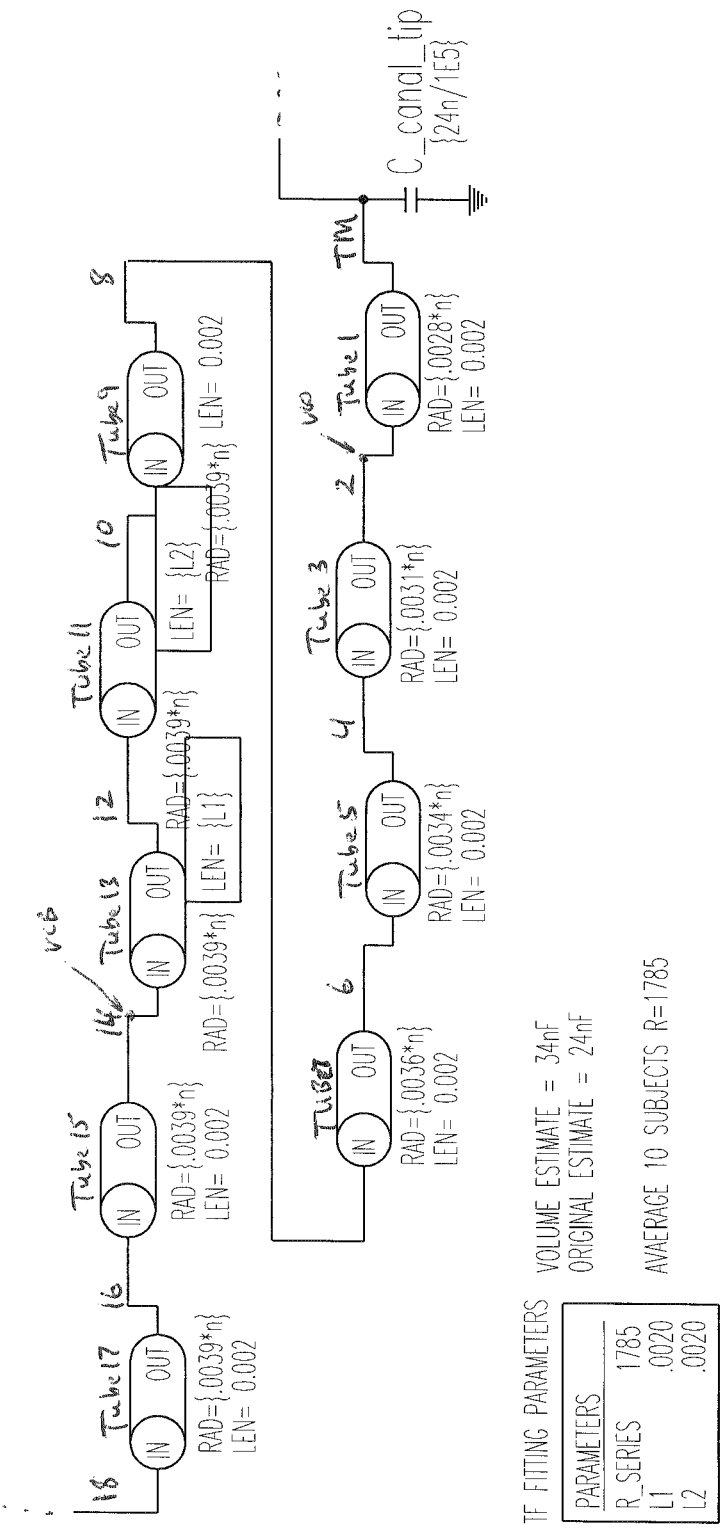
FIG. 11 is an ear canal analog, according to one embodiment of the present subject matter.

FIG. 11 is an ear canal analog, according to one embodiment of the present subject matter. The ear canal analog includes the cascade of tubes as described above in FIG. 6, and in particular the two tubes having lengths L1 and L2 and the tubes on either side with LEN=0.002. In various embodiments, 0 to 4 mm segments are compliant cavity not tube. Therefore, 4 mm offset from Stinson data may be used in various embodiments. The example of FIG. 11 is only one of many possible models and is intended to demonstrate the present subject matter. It is not intended in an exhaustive, exclusive or otherwise limiting sense.

Figure 12:
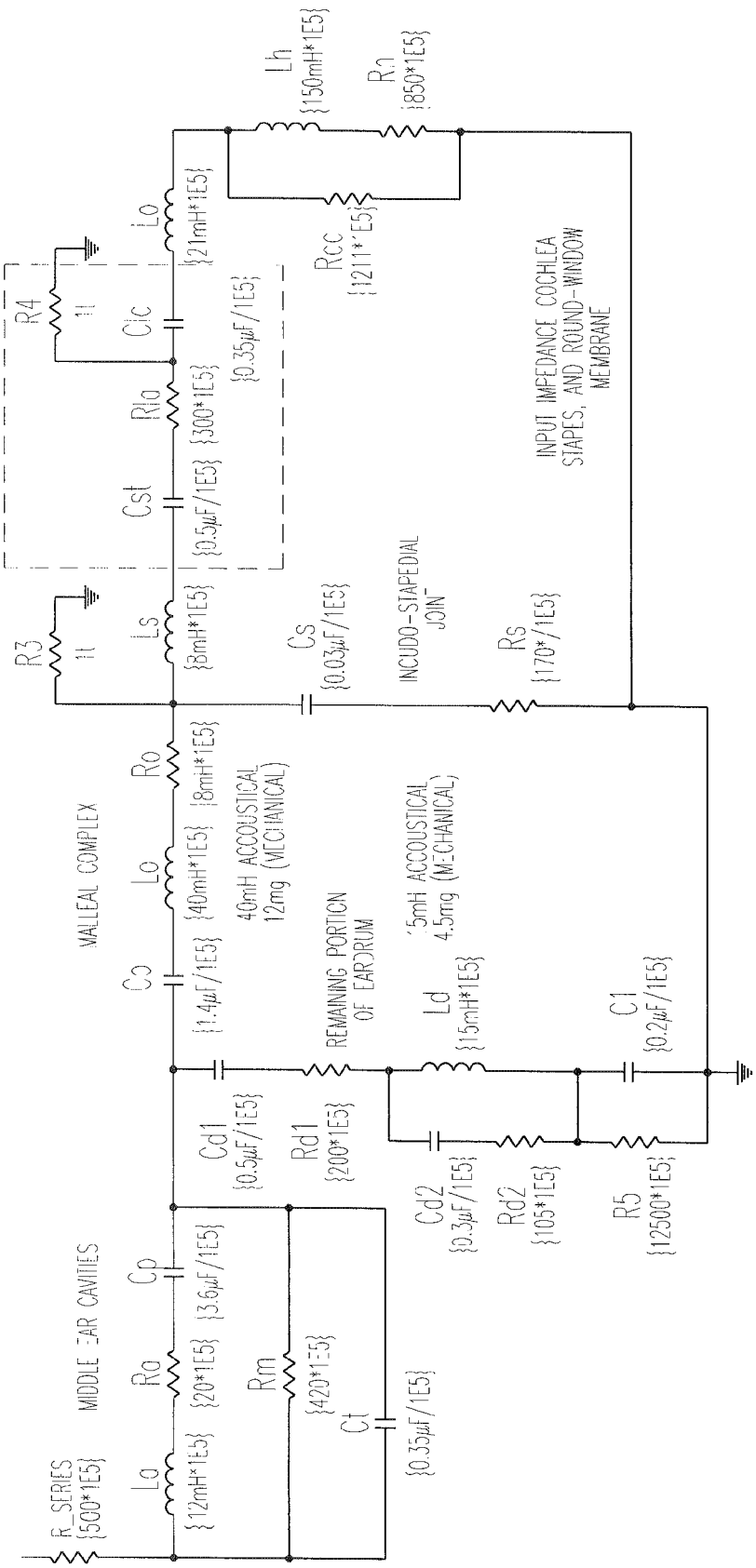
FIG. 12 is one example of a middle ear analog (Pascal et al, 1998) for use in a system, according to one embodiment of the present subject matter.

FIG. 12 is one example of a middle ear analog (Pascal et al, 1998) for use in a system according to one embodiment of the present subject matter. In the model of FIG. 12 the effective area of the eardrum is about 0.55 cm$^2$, the total area is about 0.85 cm$^2$, the thickness is about 0.01 cm (1.1 gm/cm$^3$), and total mass is about 9.35 mg. Other dimensions and masses may be modeled without departing from the scope of the present subject matter and the numbers provided herein are intended to be demonstrative and not exhaustive or exclusive or otherwise limiting.

In one embodiment, the present approach is implemented in the fitting software and the hearing device. In alternate embodiments, the present system is implemented completely in the hearing device.

In various embodiments, the present subject matter provides a method for measuring an estimated sound pressure level at a tympanic membrane in an ear canal of an ear of a wearer of a hearing assistance device using measurements away from the tympanic membrane, the method comprising: placing a sound sampling apparatus in the ear canal at a first position; placing a sound emitter in the ear canal at a second position; generating sound with the sound emitter and receiving sound with the sound sampling apparatus to measure an amplitude response of the ear canal; and determining the estimated sound pressure level at the tympanic membrane using measurements of sound from the sound sampling apparatus and the measured amplitude response. In various embodiments, the method further comprises: determining an amplitude null at a null frequency detected by the sound sampling apparatus at the first position; determining a null Q from the null frequency; determining a modeled sound pressure level at the tympanic membrane and a modeled sound pressure level at the first position using the null frequency and the null Q; and determining the estimated sound pressure level at the tympanic membrane using measurements of sound from the sound sampling apparatus at the first position, the modeled sound pressure levels at the tympanic membrane, and the modeled sound pressure levels at the first position.

Variations of the foregoing methods include wherein placing a sound sampling apparatus comprises placing a thin tube with an end at the first position for sampling sound at the first position. Variations further include placing a second end of the thin tube in a microphone port of the hearing assistance device. Variations include wherein placing a sound sampling apparatus comprises placing a microphone at the first position. In some variations the sound sampling apparatus is a microphone fitted with a small sound tube and wherein the sound emitter is a receiver. In some embodiments the first position and the second position have a minimum distance of about 5 mm. Different ways of emitting sound include, but are not limited to playing a swept audio sound into the ear canal by the hearing assistance device or playing a tone complex into the ear canal by the hearing assistance device.

In some embodiments the null Q is determined by dividing the null frequency by a measured width of the amplitude response at the null frequency.

In some embodiments the method further includes modeling the ear canal as a cascade of cylindrical tubes, each tube of the cascade of tubes having a radius and a length, the cascade of tubes including two middle lengths L1 and L2 which are calculated from: L1+L2=(5.81×105−Square Root[3.38×1011−7.92×107×(8450−$f_o$)])/(3.96×107), where $f_o$ is the null frequency; and estimating a series resistance, R, in a middle ear analog using: R=(5.92×10-3−Square Root[3.50×10-5+1.29×10-6×(2.78−Q)])/(6.46×10-7), where Q is the null Q.

Various embodiments include estimating the decibels (dB) of sound pressure level (SPL) at the tympanic membrane (TM) from: Estimated dB SPL at TM=Actual dB SPL at the first position+(Modeled dB SPL at TM−Modeled dB SPL at the first position).

The present subject matter also provides a hearing assistance device for measuring sound pressure level in an ear canal of a wearer's ear to provide the sound pressure level at a tympanic membrane of the wearer's ear including a high frequency range, comprising: a housing adapted to be worn by the wearer; a sound sampling apparatus for measuring sound in the ear canal at a first position away from the tympanic membrane; a sound emitter in the ear canal at a second position; and a processor in communication with the sound emitter and the sound sampling apparatus, the processor adapted to execute instructions to provide a measurement of the sound pressure level at the tympanic membrane of the wearer's ear using measurements of a null frequency and a null Q at the first position.

In various embodiments the sound sampling apparatus comprises a thin tube having a first end adapted to receive sound in the ear canal and a second end adapted to fit in a microphone port of the hearing assistance device. In various embodiments the sound sampling apparatus comprises a microphone fitted with a small sound tube and wherein the sound emitter is a receiver.

It is understood that the embodiments provided herein are to demonstrate the calculations, but that differences in order of the determinations or minor variations in the model of the ear canal can be made without departing from the scope of the present subject matter.

The present subject matter includes hearing assistance devices, including, but not limited to, cochlear implant type hearing devices, hearing aids, such as behind-the-ear (BTE), in-the-ear (ITE), in-the-canal (ITC), completely-in-the-canal (CIC), and receiver-in-the-canal (RIC) type hearing aids. It is understood that behind-the-ear type hearing aids may include devices that reside substantially behind the ear or over the ear. Such devices may include hearing aids with receivers associated with the electronics portion of the behind-the-ear device, or hearing aids of the type having receivers in-the-canal (RIC) or receiver-in-the-ear (RITE). It is understood that other hearing assistance devices not expressly stated herein may fall within the scope of the present subject matter.

This application is intended to cover adaptations and variations of the present subject matter. It is to be understood that the above description is intended to be illustrative, and not restrictive. The scope of the present subject matter should be determined with reference to the appended claim, along with the full scope of legal equivalents to which the claims are entitled.

What is claimed is:

1. A method for measuring an estimated sound pressure level at a tympanic membrane in an ear canal of an ear of a wearer of a hearing assistance device using measurements away from the tympanic membrane, the method comprising:
   placing a sound sampling apparatus in the ear canal at a first position;
   placing a sound emitter in the ear canal at a second position;
   generating sound with the sound emitter and receiving sound with the sound sampling apparatus to measure an amplitude response of the ear canal; and
   determining the estimated sound pressure level at the tympanic membrane using measurements of sound from the sound sampling apparatus including measurements of a null frequency and a null Q at the first position and the measured amplitude response.

2. The method of claim 1, wherein determining the estimated sound pressure level at the tympanic membrane includes:
   determining a modeled sound pressure level at the tympanic membrane and a modeled sound pressure level at the first position using the null frequency and the null Q; and
   determining the estimated sound pressure level at the tympanic membrane using measurements of sound from the sound sampling apparatus at the first position, the modeled sound pressure levels at the tympanic membrane, and the modeled sound pressure levels at the first position.

3. The method of claim 2, further comprising determining the null Q by dividing the null frequency by a measured width of the amplitude response at the null frequency.

4. The method of claim 3, further comprising:
   modeling the ear canal as a cascade of cylindrical tubes, each tube of the cascade of tubes having a radius and a length, the cascade of tubes including two middle lengths L1 and L2 which are calculated from:

$$L1+L2=(5.81\times10^5-\text{Square Root}[3.38\times10^{11}-7.92\times10^7\times(8450-f_0)])/(3.96\times10^7), \text{ where } f_0 \text{ is the null frequency; and}$$

estimating a series resistance, R, in a middle ear analog using:

$$R=(5.92\times10^{-3}-\text{Square Root}[3.50\times10^{-5}+1.29\times10^{-6}\times(2.78-Q)])/(6.46\times10^{-7}), \text{ where } Q \text{ is the null } Q.$$

5. The method of claim 2, wherein placing a sound sampling apparatus comprises placing a thin tube with an end at the first position for sampling sound at the first position.

6. The method of claim 5, further comprising placing a second end of the thin tube in a microphone port of the hearing assistance device.

7. The method of claim 2, wherein placing a sound sampling apparatus comprises placing a microphone at the first position.

8. The method of claim 2, wherein the sound sampling apparatus is a microphone fitted with a small sound tube and wherein the sound emitter is a receiver.

9. The method of claim 2, wherein the first position and the second position have a minimum distance of about 5 mm.

10. The method of claim 2, further comprising playing a swept audio sound into the ear canal by the hearing assistance device.

11. The method of claim 2, further comprising playing a tone complex into the ear canal by the hearing assistance device.

12. The method of claim 2, further comprising:
Estimating the decibels (dB) of sound pressure level (SPL) at the tympanic membrane (TM) from:

Estimated dB SPL at TM=Actual dB SPL at the first position+(Modeled dB SPL at TM−Modeled dB SPL at the first position).

13. The method of claim 1, wherein placing a sound sampling apparatus comprises placing a thin tube with an end at the first position for sampling sound at the first position.

14. The method of claim 13, further comprising placing a second end of the thin tube in a microphone port of the hearing assistance device.

15. The method of claim 1, wherein placing a sound sampling apparatus comprises placing a microphone at the first position.

16. The method of claim 1, wherein the sound sampling apparatus is a microphone fitted with a small sound tube and wherein the sound emitter is a receiver.

17. The method of claim 1, wherein the first position and the second position have a minimum distance of about 5 mm.

18. The method of claim 1, further comprising playing a swept audio sound into the ear canal by the hearing assistance device.

19. The method of claim 1, further comprising playing a tone complex into the ear canal by the hearing assistance device.

20. The method of claim 1, further comprising:
Estimating the decibels (dB) of sound pressure level (SPL) at the tympanic membrane (TM) from:

Estimated dB SPL at TM=Actual dB SPL at the first position+(Modeled dB SPL at TM−Modeled dB SPL at the first position).

21. The method of claim 1, wherein the method is performed by the hearing assistance device and a fitting system.

22. The method of claim 1, wherein the method is performed by the hearing assistance device.

* * * * *

UNITED STATES PATENT AND TRADEMARK OFFICE
CERTIFICATE OF CORRECTION

PATENT NO. : 8,542,841 B2
APPLICATION NO. : 12/685295
DATED : September 24, 2013
INVENTOR(S) : LoPresti et al.

It is certified that error appears in the above-identified patent and that said Letters Patent is hereby corrected as shown below:

On the Title Page, Item (56)

In column 2, under "Other Publications", line 2, delete "20,2010"," and insert --20, 2010",-- therefor On page 2, in column 1, under "Other Publications", line 4, delete "Pgs." and insert --pgs.--, therefor On page 2, in column 1, under "Other Publications", line 15, delete "C K," and insert --C. K.,--, therefor On page 2, in column 1, under "Other Publications", line 20, delete "H," and insert --H.,--, therefor On page 2, in column 2, under "Other Publications", line 25, delete "08/1/2/11" and insert --Dec. 08, 2011--, therefor On page 2, in column 2, under "Other Publications", line 59, delete "Pgs." and insert --pgs.--, therefor On page 2, in column 2, under "Other Publications", line 65, delete "Filed" and insert --filed--, therefor On page 2, in column 2, under "Other Publications", line 67, delete "Filed" and insert --filed--, therefor On page 2, in column 2, under "Other Publications", line 67, delete "13." and insert --13 pgs.--, therefor On page 3, in column 1, under "Other Publications", line 4, delete "Mailed" and insert --mailed--, therefor On page 3, in column 1, under "Other Publications", line 4, delete "Pgs." and insert --pgs.--, therefor Signed and Sealed this
Eighteenth Day of November, 2014

Michelle K. Lee
*Deputy Director of the United States Patent and Trademark Office*

CERTIFICATE OF CORRECTION (continued)
U.S. Pat. No. 8,542,841 B2

On page 3, in column 2, under "Other Publications", line 16, delete "J," and insert --J.,--, therefor On page 3, in column 2, under "Other Publications", line 20, delete "us" and insert --use--, therefor